(12) United States Patent  
Nurmikko et al.

(10) Patent No.: US 12,035,996 B2  
(45) Date of Patent: Jul. 16, 2024

(54) HIGH SPATIOTEMPORAL RESOLUTION BRAIN IMAGING

(71) Applicant: Brown University, Providence, RI (US)

(72) Inventors: Arto Nurmikko, Providence, RI (US); Ning Zhang, Providence, RI (US)

(73) Assignee: BROWN UNIVERSITY, Providence, RI (US)

( * ) Notice: Subject to any disclaimer, the term of this patent is extended or adjusted under 35 U.S.C. 154(b) by 290 days.

(21) Appl. No.: 16/789,203

(22) Filed: Feb. 12, 2020

(65) Prior Publication Data

US 2020/0253479 A1    Aug. 13, 2020

Related U.S. Application Data

(60) Provisional application No. 62/879,210, filed on Jul. 26, 2019, provisional application No. 62/804,462, filed on Feb. 12, 2019.

(51) Int. Cl.
*A61B 5/00* (2006.01)
*A61B 5/1455* (2006.01)
*G03H 1/04* (2006.01)

(52) U.S. Cl.
CPC .......... *A61B 5/0042* (2013.01); *A61B 5/0077* (2013.01); *A61B 5/14552* (2013.01); *A61B 5/14553* (2013.01); *A61B 5/4064* (2013.01); *G03H 1/0443* (2013.01); *G03H 1/0465* (2013.01); *A61B 2562/0242* (2013.01); *G03H 2001/0445* (2013.01); *G03H 2001/0452* (2013.01); *G03H 2001/0469* (2013.01); *G03H 2210/30* (2013.01); *G03H 2222/12* (2013.01); *G03H 2222/34* (2013.01); *G03H 2223/24* (2013.01); *G03H 2226/13* (2013.01)

(58) Field of Classification Search
CPC . A61B 5/0042; A61B 5/0077; A61B 5/14552; A61B 5/14553; A61B 5/4064; A61B 5/40
See application file for complete search history.

(56) References Cited

U.S. PATENT DOCUMENTS

| | | |
|---|---|---|
| 5,948,006 A | 9/1999 | Mann |
| 6,134,474 A | 10/2000 | Fischell et al. |

(Continued)

FOREIGN PATENT DOCUMENTS

| | | |
|---|---|---|
| CN | 101674573 B | 5/2012 |
| CN | 102480740 A | 5/2012 |

(Continued)

OTHER PUBLICATIONS

Dalla Mora, Alberto, et al. "Towards next-generation time-domain diffuse optics for extreme depth penetration and sensitivity." Biomedical optics express 6.5 (2015): 1749-1760.*

(Continued)

*Primary Examiner* — Carolyn A Pehlke

(74) *Attorney, Agent, or Firm* — Adler Pollock & Sheehan P.C.

(57) ABSTRACT

An ultra high-resolution near infrared brain imager system includes a modular cap housing closely spaced multiple vertical-cavity surface-emitting laser-single-photon avalanche photodiode array (VCSEL-SPAD) modules, each one of the VCSEL-SPAD modules including a linear VCSEL array and a SPAD detector.

6 Claims, 7 Drawing Sheets

(56) References Cited

U.S. PATENT DOCUMENTS

| | | | |
|---|---|---|---|
| 6,409,674 B1 | 6/2002 | Brockway et al. | |
| 6,754,538 B2 | 6/2004 | Linberg | |
| 7,020,505 B1 | 3/2006 | Phillips et al. | |
| 7,212,851 B2 | 5/2007 | Donoghue et al. | |
| 7,647,097 B2 | 1/2010 | Flaherty et al. | |
| 7,751,877 B2 | 7/2010 | Flaherty et al. | |
| 7,881,780 B2 | 2/2011 | Flaherty | |
| 7,901,368 B2 | 3/2011 | Flaherty et al. | |
| 7,989,936 B2 | 8/2011 | McCain | |
| 7,991,461 B2 | 8/2011 | Flaherty et al. | |
| 8,060,194 B2 | 11/2011 | Flaherty | |
| 8,095,209 B2 | 1/2012 | Flaherty | |
| 8,299,912 B2 | 10/2012 | Otto | |
| 8,386,050 B2 | 2/2013 | Donoghue et al. | |
| 8,412,302 B2 | 4/2013 | Kipke et al. | |
| 8,547,248 B2 | 10/2013 | Zdeblick et al. | |
| 8,560,041 B2 | 10/2013 | Harvey et al. | |
| 8,738,139 B2 | 5/2014 | Lanning et al. | |
| 8,812,096 B2 | 8/2014 | Flaherty et al. | |
| 8,818,498 B2 | 8/2014 | Terada et al. | |
| 8,958,868 B2 | 2/2015 | Ghovanloo et al. | |
| 9,028,405 B2 | 5/2015 | Tran | |
| 9,402,544 B2 | 8/2016 | Yee et al. | |
| 9,808,199 B2 | 11/2017 | Kilsgaard et al. | |
| 9,819,074 B2 | 11/2017 | Muller et al. | |
| 9,878,167 B1 | 1/2018 | He et al. | |
| 10,340,408 B1* | 7/2019 | Katnani | H01L 31/022408 |
| 10,433,754 B2 | 10/2019 | Nurmikko et al. | |
| 11,324,444 B2 | 5/2022 | Jensen et al. | |
| 2002/0099412 A1 | 7/2002 | Fischell et al. | |
| 2003/0216666 A1 | 11/2003 | Ericson et al. | |
| 2003/0229382 A1 | 12/2003 | Sun et al. | |
| 2004/0082875 A1 | 4/2004 | Donoghue et al. | |
| 2004/0240527 A1 | 12/2004 | Giannakis et al. | |
| 2005/0137652 A1 | 6/2005 | Cauller et al. | |
| 2005/0143790 A1 | 6/2005 | Kipke et al. | |
| 2005/0267597 A1 | 12/2005 | Flaherty et al. | |
| 2005/0283203 A1 | 12/2005 | Flaherty et al. | |
| 2006/0016753 A1 | 1/2006 | Sowemimo-Coker et al. | |
| 2006/0018990 A1 | 1/2006 | Bazzo et al. | |
| 2006/0049957 A1 | 3/2006 | Surgenor et al. | |
| 2006/0058627 A1 | 3/2006 | Flaherty et al. | |
| 2006/0094974 A1 | 5/2006 | Cain | |
| 2006/0111075 A1 | 5/2006 | Seol | |
| 2006/0149338 A1 | 7/2006 | Flaherty et al. | |
| 2006/0167371 A1 | 7/2006 | Flaherty et al. | |
| 2006/0173259 A1 | 8/2006 | Flaherty et al. | |
| 2006/0195042 A1 | 8/2006 | Flaherty | |
| 2006/0241356 A1 | 10/2006 | Flaherty | |
| 2007/0156126 A1 | 7/2007 | Flaherty | |
| 2007/0169333 A1 | 7/2007 | Donoghue et al. | |
| 2007/0265543 A1 | 11/2007 | Vansickle et al. | |
| 2008/0027347 A1 | 1/2008 | Harris et al. | |
| 2009/0157141 A1 | 6/2009 | Chiao et al. | |
| 2009/0157145 A1 | 6/2009 | Cauller | |
| 2010/0002302 A1 | 1/2010 | Duparre et al. | |
| 2010/0063411 A1 | 3/2010 | Donoghue et al. | |
| 2011/0307079 A1 | 12/2011 | Oweiss et al. | |
| 2012/0203129 A1 | 8/2012 | Rennaker | |
| 2012/0302858 A1 | 11/2012 | Kidmose et al. | |
| 2013/0079849 A1 | 3/2013 | Perryman et al. | |
| 2014/0094674 A1 | 4/2014 | Nurmikko et al. | |
| 2014/0275812 A1 | 9/2014 | Stivoric et al. | |
| 2014/0303452 A1 | 10/2014 | Ghaffari | |
| 2016/0051192 A1 | 2/2016 | Kang et al. | |
| 2016/0103487 A1 | 4/2016 | Crawford et al. | |
| 2016/0143541 A1 | 5/2016 | He et al. | |
| 2017/0014035 A1 | 1/2017 | Newberry | |
| 2017/0031441 A1 | 2/2017 | Muller et al. | |
| 2017/0171071 A1 | 6/2017 | Turon et al. | |
| 2017/0231501 A1 | 8/2017 | Culver et al. | |
| 2018/0049636 A1 | 2/2018 | Miller et al. | |
| 2018/0288717 A1 | 10/2018 | Shellhammer | |
| 2018/0333587 A1 | 11/2018 | Howard | |
| 2019/0175902 A1 | 6/2019 | Lee et al. | |
| 2019/0261860 A1 | 8/2019 | Culver et al. | |
| 2019/0336001 A1* | 11/2019 | Zhou | A61B 5/7257 |
| 2020/0036487 A1 | 1/2020 | Hammond et al. | |
| 2020/0367749 A1 | 11/2020 | Nurmikko et al. | |
| 2021/0093864 A1 | 4/2021 | Beauchamp et al. | |
| 2021/0100952 A1 | 4/2021 | Brown | |
| 2021/0275070 A1 | 9/2021 | Schuurkamp et al. | |
| 2021/0308468 A1 | 10/2021 | Shepard et al. | |
| 2021/0338127 A1 | 11/2021 | Cavuto et al. | |
| 2021/0398338 A1 | 12/2021 | Philion et al. | |
| 2022/0016774 A1 | 1/2022 | Amell et al. | |

FOREIGN PATENT DOCUMENTS

| | | |
|---|---|---|
| CN | 103169448 A | 6/2013 |
| EP | 3020450 A1 | 5/2016 |
| EP | 3150121 B1 | 10/2018 |
| JP | 2004313419 A | 11/2004 |
| JP | 2005261710 A | 9/2005 |
| JP | 2012249916 A | 12/2012 |
| JP | 2015015548 A | 1/2015 |
| JP | 6125670 B2 | 5/2017 |
| KR | 20090009940 A | 1/2009 |
| WO | 9202176 A1 | 2/1992 |
| WO | 03061517 A2 | 7/2003 |
| WO | 2008021524 A2 | 2/2008 |
| WO | 2012040401 A3 | 8/2012 |
| WO | 2016/110804 A1 | 7/2016 |
| WO | 2016187254 A1 | 11/2016 |
| WO | 2017035530 A1 | 3/2017 |
| WO | 2021016544 A1 | 1/2021 |
| WO | 2022029486 A1 | 2/2022 |

OTHER PUBLICATIONS

Blodgett, David, et al. "Brain imaging for neural tissue health assessment." Micro-and Nanotechnology Sensors, Systems, and Applications X. Vol. 10639. International Society for Optics and Photonics, 2018.*

Nolte, David D., et al. "Holographic tissue dynamics spectroscopy." Journal of Biomedical Optics 16.8 (2011): 087004.*

Saha, Sreenil. Miniaturized Optical Probes for near Infrared Spectroscopy. Diss. Ecole Polytechnique, Montreal (Canada), 2018.*

Saha, Sreenil, et al. "Compact fast optode-based probe for single-photon counting applications." IEEE Photonics Technology Letters 30.17 (2018): 1515-1518.*

Saha, Sreenil, et al. "Miniaturized probe for time-domain near-infrared spectroscopy." 2018 IEEE Biomedical Circuits and Systems Conference (BioCAS). IEEE, 2018.*

Ebeling, Karl Joachim, Rainer Michalzik, and Holger Moench. "Vertical-cavity surface-emitting laser technology applications with focus on sensors and three-dimensional imaging." Japanese Journal of Applied Physics 57.8S2 (2018): 08PA02.*

Wu, et al. Quantitative Evaluation of Atlas-Based High-Density Diffuse Optical Tomography for Imaging of the Human Visual Cortex, Biomedical Optics Express, vol. 5, 2014, pp. 3882-3900.

Rizzolatti, et al. "Motor and Cognitive Functions of the Central Premotor Cortex", Current Opinion in Neurobiology, vol. 12, 2002, pp. 149-154.

Peng, et al., "fNIRS-EEG Study of Focal Interictal Epileptiform Discharges", Epilepsy Research, vol. 108, 2014, pp. 491-505.

Ulku, et al., "A 512x512 S Spad Image Sensor with Integrated Gating for Widefield Flim", IEEE Journal of Selected Topics in Quantum Electronics, 2018, 12 pages.

Petrantonakis, et al., Single-Trial NIRS Data Classification for Brain-Computer Interfaces Using Graph Signal Processing, IEEE Transactions on Neural Systems and Rehabilitation Engineering : A Publication of the IEEE Engineering in Medicine and Biology Society, vol. 26, 2018, 10 pages.

Zhang, et al., "Coregistered Tomographic X-Ray and Optical Breast Imaging: Initial Results", Journal of Biomed Optics, vol. 10, No. 2, 2005, pp. 024033-1-024033-9.

White, et al. "Quantitative Evaluation of High-Density Diffuse Optical Tomography: In Vivo Resolution and Mapping Performance", Journal of Biomedical Optics, vol. 15, No. 2, 2010, pp. 026006-1-026006-14.

(56) References Cited

OTHER PUBLICATIONS

Zhang, et al., "Development of Motion Resistant Instrumentation for Ambulatory Near-Infrared Spectroscopy", Journal of Biomedical Optics, vol. 16, No. 8, Aug. 2011, pp. 087008-1-087008-12.
Zhang, et al., "Twenty-Four-Hour Ambulatory Recording of Cerebral Hemodynamics, Systemic Hemodynamics, Electrocardiogramd Actigraphy During People's Daily Activities", Journal of Biomedical Optics, vol. 19, No. 4, 2014, pp. 047003-1-047003-12.
Zhang, et al., "Study of Near Infrared Technology for Intracranial Hematoma Detection", Journal of Biomedical Optics, vol. 5, No. 2, 2000, pp. 206-213.
Watanabe, et al., "Noninvasive Cerebral Blood Volume Measurement During Seizures Using Multichannel Near Infrared Spectroscopic Topography", Journal of Biomedical Optics, vol. 5, No. 3, Jul. 2000, pp. 287-290.
Urban, et al., "Chronic Assessment of Cerebral Hemodynamics During Rat Forepaw Electrical Stimulation Using Functional Ultrasound Imaging", Neuroimage, vol. 101, Nov. 1, 2014, pp. 138-149.
Strangman, et al., "A Quantitative Comparison of Simultaneous BOLD fMRI and NIRS Recordings During Functional Brain Activation", Neuroimage, vol. 17, 2002, pp. 719-731.
Zhang, et al., "Adaptive Filtering to Reduce Global Interference in Non-Invasive NIRS Measures of Brain Activation: How Well and When Does It Work?", NeuroImage, vol. 45, 2009, pp. 788-794.
Strangman, et al., "Scalp and Skull Influence on Near Infrared Photon Propagation in the Colin27 Brain Template", Neuroimage, vol. 85, 2014, pp. 136-149.
Yin, et al., "Wireless Neurosensing Platform for Unconstrained Brain Research", Neuron, vol. 45, Issue 5, 2014, 13 pages.
Sen, et al., "Clinical Application of Near-Infrared Spectroscopy in Patients with Traumatic Brain Injury: a Review of the Progress of the Field", Neurophotonics, vol. 3, 2016, pp. 031409-1-031409-5.
Wyser, et al., "Wearable and Modular Functional Near-Infrared Spectroscopy Instrument with Multidistance Measurements at four Wavelengths", Neurophotonics, vol. 4, No. 4, 2017, pp. 041413-1-pp. 041413-13.
Zhang, et al., "Experimental Comparison of Using Continuous-Wave and Frequency-Domain Diffuse Optical Imaging Systems to Detect Heterogeneities", Optical Tomography and Spectroscopy of Tissue IV, Proceedings of SPIE, vol. 4250, 2001, pp. 219-238.
Torricelli, et al., "In Vivo Optical Characterization of Human Tissues from 610 to 1010 nm by Time-Resolved Reflectance Spectroscopy", Phys Med Biol, vol. 46, 2001, pp. 2227-2237.
Strangman, et al., "Depth Sensitivity and Source-Detector Separations for Near Infrared Spectroscopy Based on the Colin27 Brain Template", Aug. 2013, PLoS One, vol. 8, Issue 8, e66319, 13 pages.
Shin, et al., "Performance Enhancement of a Brain-Computer Interface Using High-Density Multi-Distance NIRS", Scientific Reports, vol. 7, 16545, 2017, 10 pages.
Villringer, et al., "Non-Invasive Optical Spectroscopy and Imaging of Human Brain Function", Trends Neuroscience, vol. 20, No. 10, 1997, pp. 435-442.
Altman, et al., "Measurement in Medicine: The Analysis of Method Comparison Studies", Journal of Royal Statistical Soc Series, vol. 32, 1983, pp. 307-317.
Bevilacqua, et al., "In Vivo Local Determination of Tissue Optical Properties: Applications to Human Brain", Applied Optics, vol. 38, No. 22, Aug. 1, 1999, pp. 4939-4950.
Bland, et al., "Agreement Between Methods of Measurement with Multiple Observations Per Individual", Journal of Biopharmaceutical Statistics, vol. 17, 2007, pp. 571-582.
Bland, et al., "Measuring Agreement in Method Comparison Studies", Statistical Methods in Medical Research, vol. 8, 1999, pp. 135-160.
Bluestone, et al., "Three-Dimensional Optical Tomography of Hemodynamics in the Human Head", Optics Express, vol. 9, No. 6, 2001, pp. 272-286.
Chu, et al., Cerebral Blood Flow on Xenon CT: Correlation with the Blood Flow Detected at the Common Carotid Artery on Ultrasonography, Kei J. Med., Suppl 1, 2000, pp. A64-A67.

Borton, et al., "An Implantable Wireless Neural Interface for Recording Cortical Circuit Dynamics in Moving Primates", Journal of Neural Engineering, vol. 10, No. 026010, 2013, 16 pages.
Chen, et al., "A Photonic Crystal Laser from Solution Based Organo-Lead Iodide Perovskite Thin Films", ACS Nano, American Chemical Society, vol. 10, No. 4, 2016, pp. 3959-3967.
Chen, et al., "Excitonic Gain and Laser Emission from Mixed-Cation Halide Perovskite Thin Films", Optica, vol. 5, No. 9, Sep. 2018, pp. 1141-1149.
Choi, et al., "Noninvasive Determination of the Optical Properties of Adult Brain: Near-Infrared Spectroscopy Approach", Journal of Biomedical Optics, vol. 9, No. 1, 2004, pp. 221-229.
Choquette, K.D., "Vertical Cavity Surface Emitting Lasers (VCSELs)", Chapter 8 in Semiconductor Lasers: Fundamentals and Applications, (Woodhead Publishing Series in Biomaterials), 2013, pp. 316-340.
Churchland, et al., "A Critique of Pure Vision", In: Computational Neuroscience Series: Large Scale Neuronal Theories of the Brain, MIT Press, 1994, pp. 22-60.
Cohen, Jacob, "A Power Primer", Psychological Bulletin, vol. 112, No. 1, 1992, pp. 155-159.
Culver, et al., "Volumetric Diffuse Optical Tomography of Brain Activity", Optics Letters, vol. 28, No. 21, Nov. 1, 2003, pp. 2061-2063.
Cunningham, et al., "Scaling Vertical Cavity Surface Emitting Laser Reliability for Petascale Systems", Applied Optics, vol. 45, No. 25, Sep. 1, 2006, pp. 6342-6348.
Duran, et al., "Compressive Imaging in Scattering Media", Optics Express, vol. 23, No. 11, May 22, 2015, pp. 14424-14433.
Eggebrecht, et al., "A Quantitative Spatial Comparison of High-Density Diffuse Optical Tomography and fMRI Cortical Mapping", Neuroimaging, vol. 61, 2012, pp. 1120-1128.
Eggebrecht, et al., "Mapping Distributed Brain Function and Networks with Diffuse Optical Tomography", Nature Photonics, vol. 8, May 18, 2014, 7 pages.
Fang, et al., "Monte Carlo Simulation of Photon Migration in 3D Turbid Media Accelerated by Graphics Processing Units", Optics Express, vol. 17, No. 22, 2009, pp. 20178-20190.
Ferrari, et al., "A Brief Review on the History of Human Functional Near-Infrared Spectroscopy (fNIRS) Development and Fields of Application", Neuroimage, vol. 63, 2012, pp. 921-935.
Firbank, et al., "Measurement of the Optical Properties of the Skull in the Wavelength Range 650-950 nm.", PhysMedBio, vol. 38, 1993, pp. 503-510.
Franceschini, et al., "Diffuse Optical Imaging of the Whole Head", Journal of Biomedical Optics, vol. 11, No. 5, 2006, pp. 054007-1-054007-10.
Geib, et al., "Fabrication and Performance of 2-Dimensional Matrix Addressable Arrays of Integrated Vertical Cavity Lasers and Resonant Cavity Photodetectors", IEEE Journal of Selected Topics in Quantum Electronics, vol. 8, No. 4, 2002, pp. 943-947.
Gramann, et al., "Cognition in Action: Imaging Brain/Body Dynamics in Mobile Humans", Rev Neuroscience, vol. 22, No. 6, 2011, pp. 593-608.
Grassi, et al., "Near-Infrared Spectroscopy and Skeletal Muscle Oxidative Function In Vivo in Health and Disease: A Review from an Exercise Physiology Perspective", Journal of Biomedical Optics, vol. 21, No. 9, Sep. 2016, pp. 091313-1-091313-20.
Gwin, et al., "Electrocortical Activity is Coupled to gait Cycle Phase During Treadmill Walking", Neuroimage, vol. 54, 2011, pp. 1289-1296.
Heelan, et al., "A Mobile Embedded Platform for High Performance Neural Signal Computation and Communication", Biomedical Circuits and Systems Conference (BioCAS), 2015, 4 pages.
Heelan, et al., "FPGA implementation of deep-learning recurrent neural networks with sub-millisecond real-time latency for BCI-decoding of large-scale neural sensors (104 nodes)", 40th Annual International Conference of the IEEE on Engineering in Medicine and Biology, 2018, pp. 1070-1073.
Hu, et al., "Ambulatory Diffuse Optical Tomography and Multimodality Physiological Monitoring System for Muscle and Exercise Applications", Journal of Biomedical Optics, vol. 21, No. 9, 2016, pp. 091314-1-091314-14.

(56) References Cited

OTHER PUBLICATIONS

Hueber, et al., "Non-Invasive and Quantitative Near-Infrared Haemoglobin Spectrometry in the Piglet Brain During Hypoxic Stress, Using a Frequency-Domain Multidistance Instrument", Physics in Medicine and Biology, vol. 46, 2001, pp. 41-62.
Huppert, et al., "A Temporal Comparison of Bold, ASL, and NIRS Hemodynamic Responses to Motor Stimuli in Adult Humans", Neuroimage, vol. 29, 2006, pp. 368-382.
Izzetoglu, et al., "Functional Near-Infrared Neuroimaging", In: Proc. 26th Annu. Int. Conf. IEEE Eng. Med. Biol. Soc., vol. 1-7, 2004, pp. 5333-5336.
Kasten, et al., "Fabrication and Characterization of Individual Addressable Vertical Cavity Surface Emitting Laser Arrays and Integrated VCSEL/PIN Detector Arrays", Proc. SPIE, vol. 6484, 2007, pp. 64840C-1-64840C-6.
Leon-Carrion, et al., "The Infrascanner, a Handheld Device for Screening in Situ for the Presence of Brain Haematomas", Brain, Injury, vol. 24, No. 10, Sep. 2010, pp. 1193-1201.
Li, et al., "Reconstructing Chromsphere Concentration Images Directly by Continuous-Wave Diffuse Optical Tomography", Optics Letters, vol. 29, No. 3, Feb. 1, 2004, pp. 256-258.
Liutkus, et al., "Imaging With Nature: Compressive Imaging Using a Multiply Scattering Medium", Scientific Reports, vol. 4, 5552, 2014, 7 pages.
Makeig, et al., "Linking Brain, Mind and Behavior", International Journal of Psychophysiology, vol. 73, 2009, pp. 95-100.
Malcolm, et al., "The Aging Brain Shows Less Flexible Reallocation of Cognitive Resources During Dual-Task Walking: A Mobile Brain/Body Imaging (MoBI) Study", Neuroimage, vol. 117, 2015, 13 pages.
Mateo, et al., "Entrainment of Arteriole Vasomotor Fluctuations by Neural Activity Is a Basis of Blood-Oxygenation-Level-Dependent "Resting-State" Connectivity", Neuron, vol. 96, No. 4, Nov. 15, 2017, 17 pages.
Mehta, et al., "Neuroergonomics: A Review of Applications to Physical and Cognitive Work", Frontiers in Human Neuroscience, vol. 7, Article 889, Dec. 2013, 10 pages.
Moreau, et al., "Near-Infrared Measurements of Brain Oxygenation in Stroke", Neurophotonics, vol. 3, No. 3, 2016, pp. 031403-1-031403-8.
Murata, et al., "Changes in Cerebral Blood Oxygenation Induced by Deep Brain Stimulation: Study by Near-Infrared Spectroscopy (NIRS)", Keio J Med, vol. 49, Suppl 1, A61-63.
Nagaoka, et al., "Development of a New Rehabilitation System Based on a Brain-Computer Interface Using Near-Infrared Spectroscopy", Adv Exp Med Biol, vol. 662, 2010, pp. 497-503.
Nemoto, et al., "Microvascular Shunts in The Pathogenesis of High Intracranial Pressure", Acta Neurochir Suppl, vol. 118, 2013, pp. 205-209.
Nurmikko, et al., "Wireless Neurotechnology for Neural Prostheses" in Neurobionics: The Biomedical Engineering of Neural Prostheses, Neurobionics: The Biomedical Engineering of Neural Prostheses, First Edition, 2016, pp. 123-161.
Okada, et al., "Theoretical and Experimental Investigation of Near-Infrared Light Propagation in a Model of the Adult Head", Applied Optics, vol. 36, No. 1, Jan. 1, 1997, pp. 21-31.
Tsow, et al. "Wearable Functional Near-Infrared (FNIR) Technology and its Applications in Naturalistic Conditions", American Journal of Biomedical Science & Research, vol. 5, No. 1, Sep. 3, 2019, pp. 33-38.
Strangman, et al., "Wearable Brain Imaging with Multimodal Physiological Monitoring", Appl Physiol, vol. 124, 2018, pp. 564-572.
Strangman, et al., "Near-Infrared Spectroscopy and Imaging for Investigating Stroke Rehabilitation: Test-Retest Reliability and Review of The Literature", Arch Phys Med Rehabil, vol. 87, Suppl 2, Dec. 2006, pp. S12-S19.
Strangman, et al., "Non-Invasive Neuroimaging Using Near-Infrared Light", Biological Psychiatry, vol. 52, 2002, pp. 679-693.
"IEEE Recommended Practice for Determining the Peak Spatial-Average Specific Absorption Rate (SAR) in the Human Head from Wireless Communications Devices: Measurement Techniques", IEEE 1528-2013, Sep. 2013, pp. 1-246.
"International Search Report and Written Opinion received for PCT Patent Application No. PCT/US2023/066014, mailed on Sep. 27, 2023", 13 pages.
"Neurological Devices", Food and Drug Administration, Aug. 4, 2021, 2 pages.
"Stratus: Changing the Way the World Looks at EEG Testing", retrieved from the link "https://stratusneuro.com/" on Sep. 9, 2023, 8 pages.
Office Action Received for CN Patent Application No. 201280024098.3, dated Mar. 18, 2015, 9 pages.
Ahn, et al., "Optimal Design of Wireless Power Transmission Links for Millimeter-Sized Biomedical Implants", IEEE Transactions on Biomedical Circuits and Systems, vol. 10, No. 1, Feb. 2016, pp. 125-137.
Behzad, et al., "The Role of EEG in the Diagnosis and Management of Patients with Sleep Disorders", Journal of Behavioral and Brain Science, vol. 11, Oct. 19, 2021, pp. 257-266.
Benovitski, et al., "Ring and Peg Electrodes for Minimally-Invasive and Long-Term Sub-Scalp EEG Recordings", Epilepsy Research, vol. 135, 2017, pp. 29-37.
Biederman, et al., "A Fully-Integrated, Miniaturized (0.125 $mm^2$) 10.5 µW Wireless Neural Sensor", IEEE Journal of Solid-State Circuits, vol. 48, No. 4, Apr. 2013, pp. 960-970.
Chestek, et al., "HermesC: Low-Power Wireless Neural Recording System for Freely Moving Primates", IEEE Transactions on Neural Systems and Rehabilitation Engineering, vol. 17, No. 4, Aug. 1, 2009, pp. 330-338.
Duun-Henriksen, et al., "EEG Signal Quality of a Subcutaneous Recording System Compared to Standard Surface Electrodes", Journal of Sensors, vol. 2015, Article ID 341208, 2015, 10 pages.
England, et al., "Epilepsy Across the Spectrum: Promoting Health and Understanding", Institute of Medicine (US) Committee on the Public Health Dimensions of the Epilepsies. Washington (DC): National Academies Press (US); 2012. The National Academies Collection: Reports funded by National Institutes of Health., 2012, 568 pages.
Extended European Search Report Received for EP Patent Application No. EP12758264.1, dated Sep. 1, 2014, 9 pages.
EPC, "Time-of-Flight Chips", Espros Photonics Corporation, Retrieved on Feb. 28, 2024, Available at <https://www.espros.com/sensor-products/chips/time-of-flight-chips/>, 5 pages.
Fang, et al., "Ultrathin, Transferred Layers of Thermally Grown Silicon Dioxide as Biofluid Barriers for Biointegrated Flexible Electronic Systems", Proceedings of the National Academy of Science, vol. 113, No. 42, Oct. 18, 2016, pp. 11682-11687.
Gao, et al., "A Theory of Multineuronal Dimensionality, Dynamics and Measurement", bioRxiv, Nov. 11, 2017, pp. 1-50.
Ghamari, et al., "A Survey on Wireless Body Area Networks or eHealthcare Systems in Residential Environments", Sensors, vol. 16, Issue 6, Jun. 7, 2016, 34 pages.
Gliske, et al., "Variability in the Location of High Frequency Oscillations During Prolonged Intracranial EEG Recordings", Nature Communications, vol. 9, No. 2155, 2018, 14 pages.
Granata, et al., "Management of the Patient with Medically Refractory Epilepsy", Expert Review of Neurotherapeutics, vol. 9, No. 12, Dec. 2009, pp. 1791-1802.
Handa, et al., "Open and Free EEG Datasets for Epilepsy Diagnosis", arXiv preprint arXiv:2108.01030v1, Aug. 2, 2021, 6 pages.
Hao, et al., "Wireless Body Sensor Networks for Health-Monitoring Applications", Physiological Measurement, vol. 29, Issue 11, Oct. 9, 2008, pp. R27-R56.
Harrison, et al., "A Low-Power Integrated Circuit for a Wireless 100-Electrode Neural Recording System", IEEE Journal of Solid-State Circuits, vol. 42, No. 1, 2007, pp. 123-133.
Harrison, et al., "A Low-Power Low-Noise CMOS Amplifier for Neural Recording Applications", IEEE Journal of Solid-State Circuits, vol. 38, No. 6, 2003, pp. 958-965.
Harrison, et al., "Wireless Neural Recording With Single Low-Power Integrated Circuit", IEEE Transactions on Neural Systems and Rehabilitation Engineering, vol. 17, No. 4, Aug. 1, 2009, pp. 322-329.

(56) References Cited

OTHER PUBLICATIONS

Hochberg, et al., "Neuronal Ensemble Control of Prosthetic Devices by a Human with Tetraplegia", Nature, vol. 442, No. 7099, 2006, pp. 164-171.
Houmani, et al., "Diagnosis of Alzheimer's Disease with Electroencephalography in a Differential Framework", PLoS One, vol. 13, No. 3, e0193607, Mar. 20, 2018, pp. 1-19.
Ibrahim, et al., "Safe Inductive Power Transmission to Millimeter-Sized Implantable Microelectronics Devices", 37th Annual International Conference of the IEEE Engineering in Medicine and Biology Society (EMBC), 2015, pp. 817-820.
Jeong, et al., "3-D Hermetic Packaging of Sub-mm Size Implantable Microelectronic Sensors by Atomic Layer Deposition (ALD) for Chronic Use", 2018, 1 page.
Jeong, et al., "Conformal Hermetic Sealing of Wireless Microelectronic Implantable Chiplets by Multilayered Atomic Layer Deposition (ALD)", Advanced Functional Materials, vol. 29, No. 1806440, 2018, pp. 1-10.
Kiani, et al., "Design and Optimization of a 3-Coil Inductive Link for Efficient Wireless Power Transmission", IEEE Transactions on Biomedical Circuits and Systems, vol. 5, No. 6, Dec. 2011, pp. 579-591.
Lecomte, et al., "Silk and Peg as Means to Stiffen a Parylene Probe for Insertion in the Brain: Toward a Double Time-Scale Tool for Local Drug Delivery", Journal of Micromechanics and Microengineering, vol. 25, No. 12, Oct. 19, 2015, pp. 1-12.
Lee, et al., "A Scalable and Low Stress Post-CMOS Processing Technique for Implantable Microsensors", Micromachines, vol. 11, No. 925, 2020, pp. 1-15.
Lee, et al., "An Implantable Wireless Network of Distributed Microscale Sensors for Neural Applications", 2019 9th International IEEE/EMBS Conference on Neural Engineering (NER),, 2019, pp. 871-874.
Lee, et al., "Asynchronous Large-Scale Networks for Spatially Distributed Autonomous Wireless RF Event Sensors", Under review at Nature Portfolio, posted on Oct. 13, 2022, 20 pages.
Lee, et al., "Neural Recording and Stimulation Using Wireless Networks of Microimplants", Nature Electronics, vol. 4, Aug. 2021, pp. 604-614.
Lee, et al., "Wireless Power and Data Link for Ensembles of Sub-mm scale Implantable Sensors near 1GHz", 2018 IEEE Biomedical Circuits and Systems Conference (BioCAS)., 2018, pp. 1-4.
Leung, et al., "A CMOS Distributed Sensor System for High-Density Wireless Neural Implants for Brain-Machine Interfaces", ESSCIRC 2018—IEEE 44th European Solid State Circuits Conference (ESSCIRC)., 2018, pp. 230-233.
Minnikanti, et al., "Lifetime Assessment of Atomic-Layer-Deposited Al2O3-Parylene C Bilayer Coating for Neural Interfaces using Accelerated Age Testing and Electrochemical Characterization", Acta Biomaterialia, vol. 10, Issue 2, Feb. 2014, pp. 960-967.
Moctezuma, Luis Alfredo, "Towards Universal EEG Systems with Minimum Channel Count Based on Machine Learning and Computational Intelligence", Doctoral theses at Norwegian University of Science and Technology, Trondheim, Aug. 2021, 178 pages.
Moradi, et al., "Antenna Design for Implanted Tags in Wireless Brain Machine Interface System", IEEE Antennas and Propagation Society International Symposium, 2013, pp. 2083-2084.
Naik, et al., "Intelligent Communication Module for Wireless Biosensor Networks", Biosensors, Chapter 13, Feb. 2010, pp. 225-240.
Neely, et al., "Recent Advances in Neural Dust: Towards a Neural Interface Platform", Current Opinion in Neurobiology, vol. 50, Jun. 2018, pp. 64-71.
Oto, Maria Meritxell, "The Misdiagnosis of Epilepsy: Appraising Risks and Managing Uncertainty", Seizure, vol. 44, 2017, pp. 143-146.
Patterson Iii, et al., "CMOS ICs for Brain Implantable Neural Recording Microsystems", Applications of CMOS circuits in Biology, R. Westervelt and H. Lee Eds., 2007, pp. 259-291.
International Search Report and Written Opinion Received for PCT Patent Application No. PCT/US2012/029664, dated Jul. 18, 2012, 9 pages.
PCT/US2019/042051, "International Search Report and Written Opinion dated received for PCT Patent Application No. PCT/US2019/042051, mailed on Nov. 1, 2019", Nov. 1, 2019, 10 pages.
Piyare, et al., "On-Demand LoRa: Asynchronous TDMA for Energy Efficient and Low Latency Communication in IoT", Sensors, vol. 18, No. 3718, Nov. 1, 2018, pp. 1-22.
Ramrakhyani, et al., "Design and Optimization of Resonance-Based Efficient Wireless Power Delivery Systems for Biomedical Implants", IEEE Transactions on Biomedical Engineering, vol. 5, No. 1, Feb. 2011, pp. 48-63.
Rishani, et al., "Wearable, Epidermal and Implantable Sensors for Medical Applications", retrieved from the linkhttps://arxiv.org/abs/1810.00321, Sep. 30, 2018, 48 pages.
Shankar, et al., "Energy-Efficient Protocols for Wireless Communication in Biosensor Networks", IEEE, 12th IEEE International Symposium on Personal, Indoor and Mobile Radio Communications, PIMRC, 2001, pp. D114-D118.
Sigurdsson, et al., "A Method for Large-Scale Implantation of 3D Microdevice Ensembles into Brain and Soft Tissue", Microsystems & Nanoengineering, vol. 6, Article No. 97, 2020, pp. 1-13.
Sigurdsson, et al., "Distributed Delivery of Intracortical Microdevices", 2018, 1 page.
Song, et al., "A Brain Implantable Microsystem With Hybrid RF/IR Telemetry for Advanced Neuroengineering Applications", Proc. 29th Ann. Int. Conf. IEEE EMBS, 2007, pp. 445-448.
Song, et al., "Development of a Chipscale Integrated Microelectrode/Microelectronic Device for Brain Implantable Neuroengineering Applications", IEEE Transactions on Neural Systems and Rehabilitation Engineering vol. 13, No. 2, 2005, pp. 220-226.
Stirling, et al., "Seizure Forecasting Using a Novel Sub-Scalp Ultra-Long Term EEG Monitoring System", Frontiers in Neurology, vol. 12, Article 713794, Aug. 2021, 11 pages.
Tatum, IV, William O., "Long-Term EEG Monitoring: A Clinical Approach to Electrophysiology", Journal of Clinical Neurophysiology, vol. 18, No. 5, 2001, pp. 442-455.
Tomer, et al., "Advanced CLARITY for Rapid and High-Resolution Imaging of Intact Tissues", Nature Protocols, vol. 9 No. 7, Jul. 2014, pp. 1682-1697.
Uchitel, et al., "Wearable, Integrated EEG-fNIRS Technologies: A Review", Sensors, vol. 21, No. 6106, Sep. 12, 2021, 19 pages.
Weisdorf, et al., "Ultra-Long-Term Subcutaneous Home Monitoring of Epilepsy—490 Days of EEG from Nine Patients", Epilepsia, vol. 60, 2019, pp. 2204-2214.
Xie, et al., "Plasma-Assisted Atomic Layer Deposition of Al2O3 and Parylene C Bi-Layer Encapsulation for Chronic Implantable Electronics", Applied Physics Letters, vol. 101, 2012, pp. 093702-1-093702-5.
Yakovlev, et al., "Implantable Biomedical Devices: Wireless Powering and Communication", IEEE Communications Magazine, vol. 50, No. 4, Apr. 2012, pp. 152-159.
Yang, et al., "8.3 A 553F2 2-Transistor Amplifier-Based Physically Unclonable Function (PUF) with 1.67% Native Instability", IEEE International Solid-State Circuits Conference (ISSCC), Feb. 2017, pp. 146-147.
Yeon, et al., "Microfabrication, Assembly, and Hermetic Packaging of Mm-Sized Free-Floating Neural Probes", IEEE Biomedical Circuits and Systems Conference, 2017, pp. 1-4.
Yetisen, et al., "Wearables in Medicine", Advanced Materials, vol. 30, Article1706910, 2018, 26 pages..
Yin, et al., "A 100-Channel Hermetically Sealed Implantable Device for Chronic Wireless Neurosensing Applications", IEEE Trans. on Biomedical Circuits and Systems, vol. 7, No. 2, Apr. 2013, pp. 115-128.
Zack, et al., "National and State Estimates of the Numbers of Adults and Children with Active Epilepsy—United States, 2015", MMWR Morbidity and Mortality Weekly Report, vol. 66, No. 31, Aug. 11, 2017, pp. 821-825.
Zhang, et al., "EEG/MEG Based Diagnosis for Psychiatric Disorders", Frontiers in Human Neuroscience, Editorial article, Nov. 2, 2022, 3 pages.

(56) References Cited

OTHER PUBLICATIONS

"International Search Report and Written Opinion received for PCT Patent Application No. PCT/US2023/078505, mailed on Apr. 10, 2024", 11 pages.

* cited by examiner

HIGH SPATIOTEMPORAL RESOLUTION BRAIN IMAGING

CROSS REFERENCE TO RELATED APPLICATIONS

This application claims benefit from U.S. Provisional Patent Application Ser. No. 62/804,462, filed Feb. 12, 2019, and U.S. Provisional Patent Application Ser. No. 62/879,210, filed Jul. 26, 2019, each of which are incorporated by reference in their entirety.

STATEMENT REGARDING GOVERNMENT INTEREST

None.

BACKGROUND OF THE INVENTION

The present invention generally relates to brain imaging, and more specifically to high spatiotemporal resolution brain imaging.

The non-invasive recording and analysis of human brain activity during sensing, decision making, and actions in natural, mobile working conditions is a central challenge in Neurotechnology research. The Brain Research through Advancing Innovative Neurotechnologies® (BRAIN) Initiative is aimed at revolutionizing the understanding of the human brain. By accelerating the development and application of innovative technologies, researchers will be able to produce a revolutionary new dynamic picture of the brain that, for the first time, shows how individual cells and complex neural circuits interact in both time and space.

The BRAIN Initiative is rapidly advancing the state-of-the-art in brain imaging capabilities, including cellular tagging and imaging and the ability to image new molecular species deep within the brain. To date, however, a major topic of the BRAIN initiative has been under-represented, i.e., behaviorally active human neuroimaging that allows for movement in space/place during imaging in more natural environments while maintaining high resolution. Enabling users to wear compact unobtrusive neural sensing/imaging devices represents a new neurotechnology space.

SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In general, in one aspect, the invention features an ultra high-resolution near infrared brain imager system including a modular cap housing closely spaced multiple vertical-cavity surface-emitting laser-single-photon avalanche photodiode array (VCSEL-SPAD) modules, each one of the VCSEL-SPAD modules including a linear VCSEL array and a SPAD detector.

In another aspect, the invention features a system including a source of light, the source of light including a semiconductor laser diode array configured to generate light over a period of time, a beamsplitter, a cortical target, and a detector, the detector including a solid-state photodetector array and configured detect light direct light reflected over the period of time from the beamsplitter and the cortical target and generate a composite image.

In another aspect, the invention features method including providing a source of light, the source of light comprising semiconductor laser diode array, providing a beamsplitter for partioning the laser emission into primary beam and reference beam, providing a cortical target, providing a detector, the detector including a time-gated solid-state photodetector array, generating light over a period of time from the source of light, splitting the generated light from the beamsplitter to the cortical target and the detector, and generating a composite, coherent hologram in the detector, the composite hologram resulting from a summation of slightly different optical pathways reflecting from the cortical target at different angles for individual laser-detector element pair.

In another aspect, the invention features an imaging system including an integration of vertical-cavity surface-emitting lasers, single-photon avalanche photodiodes, and coherent high time resolution detection techniques to enhance a spatial resolution, sensitivity/depth penetration, and chromophore quantification capabilities of a mobile NIRS device.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

These and other features, aspects, and advantages of the present invention will become better understood with reference to the following description, appended claims, and accompanying drawings where:

DETAILED DESCRIPTION

Figure 1A:
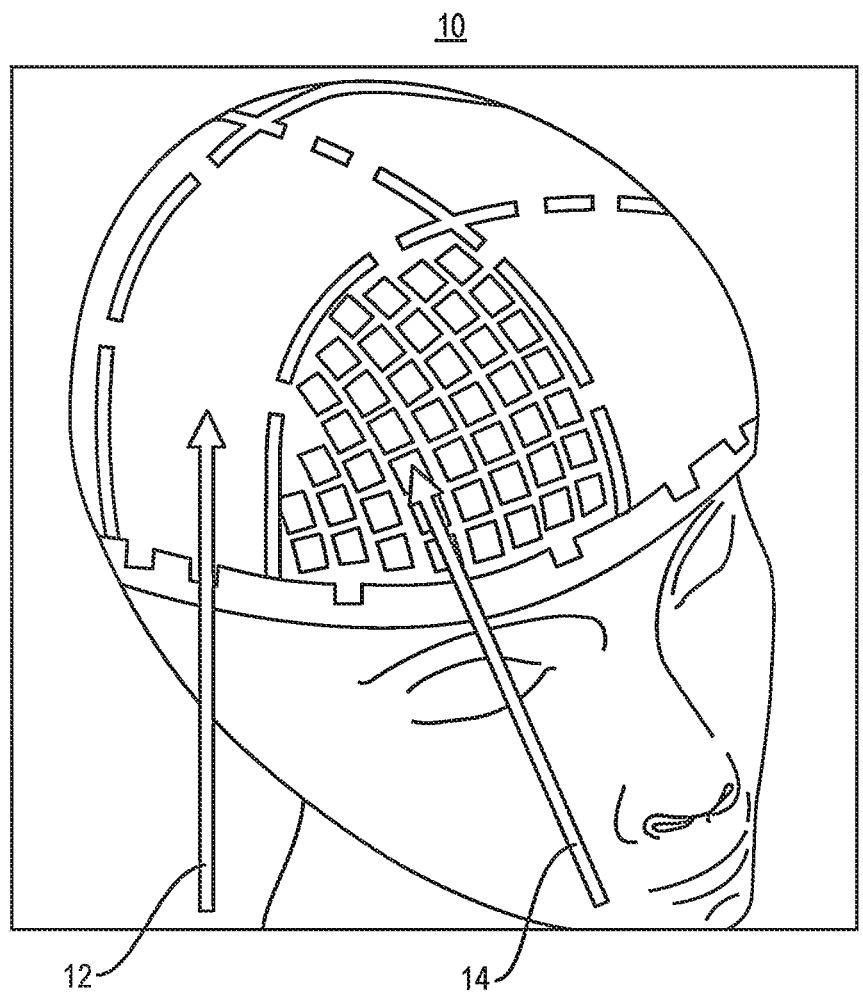
FIG. 1A is a diagram of an exemplary ultra high-resolution near infrared brain imager system.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

Because human tissue is sufficiently transparent to near-infrared (NIR) wavelengths (650-950 nm), near-infrared spectroscopy (NIRS) can be used to non-invasively monitor brain oxygenation and perfusion. NIR light is non-ionizing and does not harm biological tissue at the 1-4 mW/cm2 average power densities customarily utilized. Moreover, NIR wavelengths are easily achieved using semiconductor laser diodes. By using multiple NIR wavelengths, one can measure oxy-hemoglobin (O2Hb), deoxy-hemoglobin (HHb), and total-hemoglobin (HbT) concentrations. Given multiple overlapping NIRS measurements, diffuse optical tomography (DOT) reconstruction techniques can be used to generate 2D or 3D images of the same cerebral variables. Temporal resolution can be upwards of 20 Hz. NIRS imaging technologies can also be made low-cost to facilitate future research and clinical applications.

The slow clinical adoption of NIRS approaches arises because of core issues regarding the spatial resolution, depth penetration (sensitivity), and quantification capabilities of NIRS-based brain measurements.

While a ~5 mm spatial resolution may be achievable based on theoretical investigations of light diffusion through tissue, it is rarely achieved in practice. NIRS spatial resolution often remains >15-20 mm, making it clinically unacceptable. Improving spatial resolution to 3 mm or less would enable more precise delineations of stroke margins or TBI brain-function gains, or more accurate identification of cortical epileptic foci.

NIRS-based depth penetration has typically been limited to the outermost ~10 mm of brain tissue. This limit is fundamentally based on the detector's sensitivity, dynamic range, and noise-floor. Many detectors (particularly for mobile devices) have poor sensitivity and/or poor dynamic range. Depth penetration is a major concern for many clinicians as Alzheimer's and Parkinson's disease, epilepsy, depression and other conditions exhibit dysfunction in deeper brain tissues.

Continuous wave (CW)-NIRS systems can only measure relative in chromophore concentrations, not absolute concentrations. For example, blood pressure measurements that are only relative (indicating higher or lower than the previous measurement) would be of limited use, which is precisely the situation with CW-NIRS today. In contrast, absolute quantification of cerebral oxy- and deoxy-hemoglobin concentrations enables direct comparisons between recordings taken anytime—which could be used for monthly rehabilitation monitoring, weekly drug-efficacy assessment, and chronic disease progression evaluations, among others. Time-domain (TD) NIRS techniques are optimal for calculating absolute chromophore concentrations, but the ultrafast lasers and ultrafast detectors required are large instruments which have not been compatible with mobile device development.

The above three issues have been the Achilles heel of NIRS-based techniques for decades, and are showstoppers for NIRS clinical adoption. The present invention helps solve these long-standing problems in laboratory NIRS systems. One important aspect of the present invention is the compactness and wearability of the device which enables a user's mobility and measurements in many different point-of-care types of settings: office visits, home, and during daily mobile activities.

As shown in FIG. 1A, an exemplary ultra high-resolution near infrared brain imager system 10 includes a modular cap 12 housing closely spaced multiple vertical-cavity surface-emitting laser-single-photon avalanche photodiode array (VCSEL-SPAD) modules 14. The modular cap 12 is worn immediately adjacent to a skull.

Figure 1B:
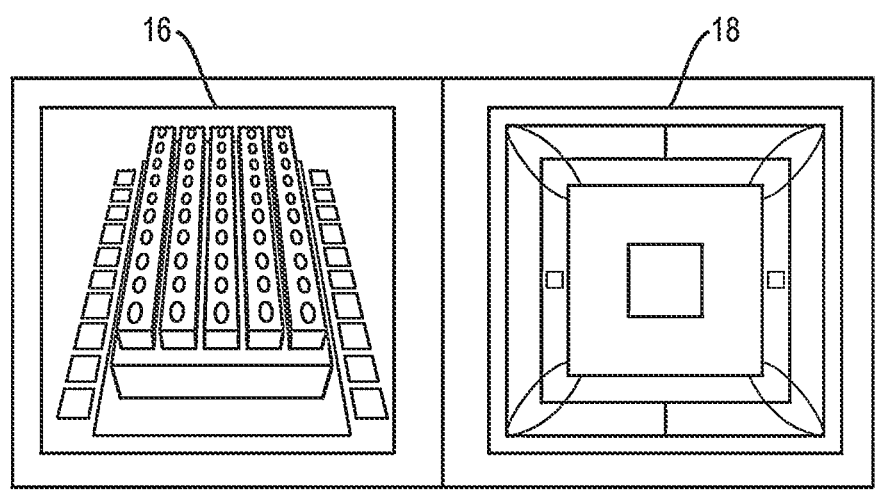
FIG. 1B is a diagram of an exemplary VCSEL-SPAD module.

As shown in FIG. 1B, each one of the VCSEL-SPAD modules includes a linear VCSEL array 16 and a SPAD detector 18.

The ultra high-resolution near infrared brain imager system 10 captures cutting-edge photonics technologies to integrate high density planar, ultracompact semiconductor surface emitting laser (VCSEL) arrays 16 with ultra-fast, time gated single-photon avalanche photodiodes (SPADs) 18 into a portable implementation. System 10 selects only those photons undergoing minimal scattering in tissue (termed "sub-diffuse light") by exploiting time-reversal symmetry principles. Given that the source array element proximities are on the scale of the photon mean free path in tissue (~100 m), computing cross-channel correlations adds important information to the average return signals detected from targeted volumes of the brain, thereby enhancing spatiotemporal resolution. Computing cross-correlations for high channel counts in turbid media requires statistical approaches which, for mobile use, require high data rate, secure, wireless telecommunication links to decoding computers running model algorithms.

The ultra high-resolution near infrared brain imager system 10 is the emergence of high-efficiency vertical-cavity surface-emitting laser (VCSEL) 2-dimensional arrays. VCSELs with ~10 m sized individual elements with array element separation as small as 20 µm, can have electrical-to-optical conversion efficiencies exceeding 50% and provide high power, coherent narrow-band wavelength output. Moreover, VCSELs can be switched on-off at speeds equivalent to many GHz and are highly reliable and low cost. The utilization of VCSELs arrays may achieve a 1000-fold increase in source density to overcome the resolution limits of standard NIRS.

Complementing VCSEL array technology is the SPADs. These ultra-high performance detectors enable photon counting as well as sub-nanosecond time-gating, thus being capable of time-domain (TD) measurements with sub-nsec gating of thousands of detector SPAD elements (pixels) packed into a small active camera area (<10 mm$^2$)]. Cutting edge silicon CMOS SPADs have high quantum efficiencies even in the NIR (>30%), coupled with active protection circuits to prevent sensor burnout due to exposure to excess ambient light, as is expected in any wearable or mobile setting. The high density, spatially proximate combination of VCSEL arrays and SPADs can greatly enhance human brain imaging.

The highest density NIRS approaches for adult human brain imaging use SD spacings ~13 mm, leading to a spatial resolution ~13 mm. The ultra high-resolution near infrared brain imager system 10 makes changes to the "standard" NIRS approach to significantly improve the spatial resolution and quantitation for non-invasive mobile NIRS in adult humans. The ultra high-resolution near infrared brain imager system 10 uses semiconductor vertical cavity surface emitting laser (VCSEL) arrays that emit in the infrared. For increased sensitivity, the number of wavelengths can be scaled up by integration of multiple VCSEL die. The resulting compact microelectronic/microphotonic component provide a narrow-band, ultra-high-density (UHD) light source for NIRS applications, which is then be combined in various geometries to make them suitable for human brain imaging. The high density of light sources improves spatial resolution, whereas the high speed of these light sources enables improved chromophore quantitation. The capabilities of these light sources, coupled with high-performance detectors, provide additional NIRS capabilities.

Of the currently available NIRS detector technologies-silicon photodiodes (SPDs), avalanche photodiodes (APDs), photomultiplier tubes (PMTs), and camera/imaging sensors—the fastest and most sensitive are PMTs. These, however, are also bulky and not compatible with mobile use. The ultra high-resolution near infrared brain imager system 10 uses single-photon avalanche diodes (SPADs) for detection.

Photographic imaging is based on single scattering events, whereas non-invasive DOT of the brain is based on tomographic reconstruction of light undergoing many scattering events and analyzed via diffusion approximation to the radiative transport equation. Significantly less attention has been paid to the photonics regime of "few scattering events", or the "sub-diffuse regime". Optical coherence tomography (OCT) does operate in this regime and generates very high-resolution imaging below tissue surfaces. However, the depth of penetration of OCT is on the order of 1 mm, making it less useful for non-invasive human brain imaging. The ultra high-resolution near infrared brain imager system 10 combines temporally short (~100 psec) pulses from the VCSEL sources plus rapid gating of SPAD detectors (~20 psec) to "select" for photons undergoing few (<5-10) scattering events by windowing in time. Given the fixed speed of light, such photons can only reach a limited range of locations within tissue and hence intrinsically represent signals from a more spatially localized region than fully diffuse light. In addition, a beamsplit light path is also transmitted to the detector to enable coherent detection.

For the data driven models, the ultra high-resolution near infrared brain imager system 10 uses machine learning tools to extract local neurovascular signals from acquired coherently detected imagery. We leverage a wireless wearable computational platform which embeds FPGA-fabric to implement customized algorithms for decoding of large scale MIMO (neural data), via wireless telemetry.

In summary, the ultra high-resolution near infrared brain imager system 10 uses (1) VCSEL arrays—as an ultra-high-density, high-performance light sources—plus (2) photon counting (SPAD) detectors and (3) the coherent-detection, time-domain approach to allow us to conduct non-invasive NIRS measurements in the "sub-diffuse regime" of 1-10 photon scattering events. The extremely small VCSELs facilitate their use for high-density mobile imaging. When combined with high-speed and optimal (single-photon) sensitivity of SPAD detectors, this next-generation, high-sensitivity/high-density prototype is expected to achieve <1 mm effective resolution with substantially deeper depth penetration, as well as absolute quantitation of chromophore concentrations.

The ultra high-resolution near infrared brain imager system 10 adapts cutting-edge semiconductor optoelectronics to build an ultrahigh density, fast time-gated multichannel source-detector infrared system that significantly improves the spatiotemporal resolution of any current or pending functional NIRS approaches.

Figure 2:
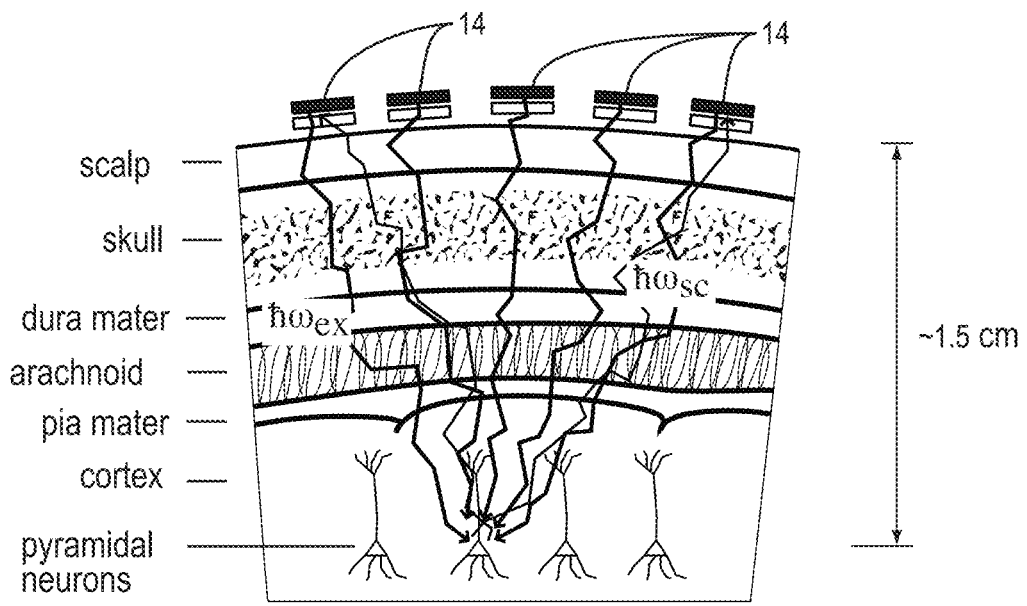
FIG. 2 is an illustration of photon diffusion.

In FIG. 2, an illustration of photon diffusion to access a cortical target through scalp and by the closely spaced multiple vertical-cavity surface-emitting laser-single-photon avalanche photodiode array (VCSEL-SPAD) modules 14 is shown. We used photon migration simulations in a detailed adult human head model to investigate the sensitivity and spatial resolution and point-spread functions of our geometry, including the analysis of photon cross-correlations in a multichannel MIMO-geometry from simulated time-of flight data. We developed an optical subsystem to enable MIMO implementation of high density source-detector arrays for turbid media. The ultra high-resolution near infrared brain imager system 10 device design enables access to subdiffusive hemodynamic imaging regime with very short interchannel source-detector elements, on the scale of the photon mean free path in tissue. The VCSEL arrays are based of customized linear arrays of sub-nsec pulsed VCSEL arrays (at 200 m pitch) with different output wavelengths (780 nm and 850 nm) first with coherent detection by a single element SPAD, and then with a fully time gated imaging SPAD camera. We incorporate measurement units with integrated micro-optical components into a flexible cap suitable for human use.

Conventional NIRS photon transport from source to detectors takes place purely in the diffusive transport regime so that imaging fine vasculature is not possible. We exploit the close-packing of sub-mm sized VCSEL-photodiode pairs to acquire images of cortical microvasculature.

Figure 3:
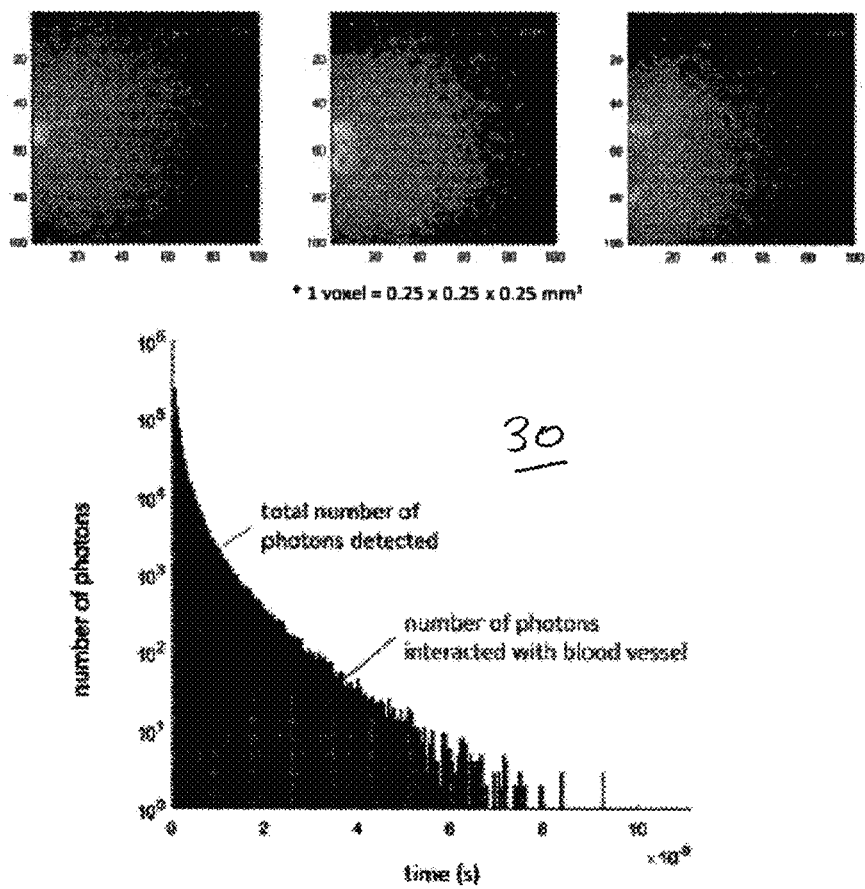
FIG. 3 illustrates exemplary simulation results.

In FIG. 3, exemplary simulation results 30 are illustrated using general purpose GPU based Monte Carlo simulations with massively parallel computing algorithm suggest that ultrafast time-gating can significantly enhance sensitivity of a specific tissue structures (in this case, surface blood vessels) by more than two orders of magnitude for single wavelength. This suggests that a large number of closely packed photon transport channels (and corresponding large source-detector reflection matrices) can extend NIRS imaging of the cortical vasculature at sub-mm resolution, a regime not previously considered possible.

We extended these simulations to focus propagation from scalp-skull-CSF-cortex and back for up to 256 time resolved optical source-detector channels with 50 m spacings. We analyzed cross-channel information in subdiffusive photon detection (i.e., nearly ballistic photons in small FOV) and applied "decoding algorithms" to enhance optically imaged signals which directly relate to spatiotemporal features relevant to targeted brain activity.

Figure 4:
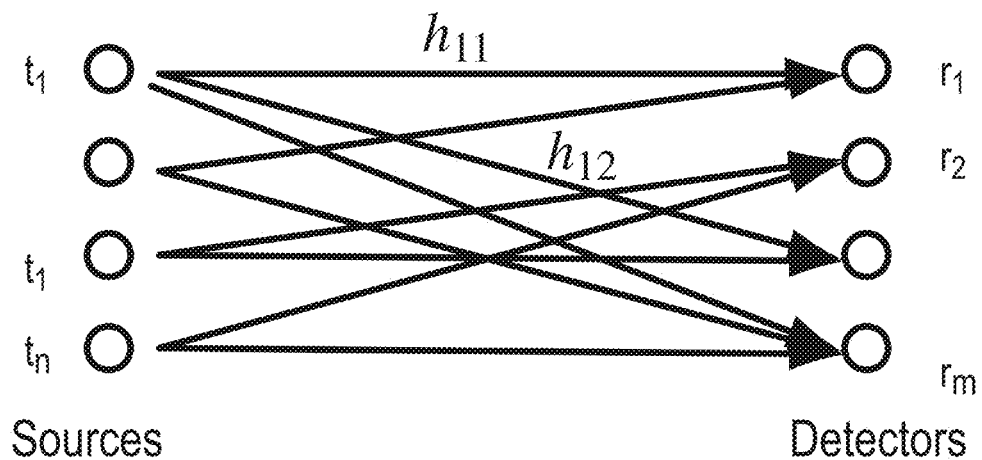
FIG. 4 is an exemplary block diagram of a generic MIMO electromagnetic network.

In FIG. 4, an exemplary block diagram of a generic MIMO electromagnetic network 40 is illustrated. The network shows a MIMO source-receiver arrangement where the transmitter elements (source) $t_i$ connect to received (detector) signals $r_i$ via the model specific transfer matrix $h_{ij}$+noise. Here individual source elements and receiver elements, respectively are within the mean free path for the photons (on the order of 100 m, e.g., tissue). We noted the analog to statistical techniques in decoding neural data acquired from multielement (e.g., intracortical microelectrode) electrophysiological recordings. However, the situation encountered here needs both optical and neurocomputational analysis, respectively: dual-layered situation: first, extraction of fast cross-correlation matrix elements hij in MIMO analysis (fast<msec, i.e., static on neural response timescale) for enhanced subdiffusive photon detection; and second, developing compatible decoding algorithms (on >msec scale) for optically imaged signals to extract features relevant to targeted brain activity such as field potentials in the cortex. For the data driven models, we explored machine learning tools to extract local neurovascular signals from acquired coherently detected imagery.

Figure 5:
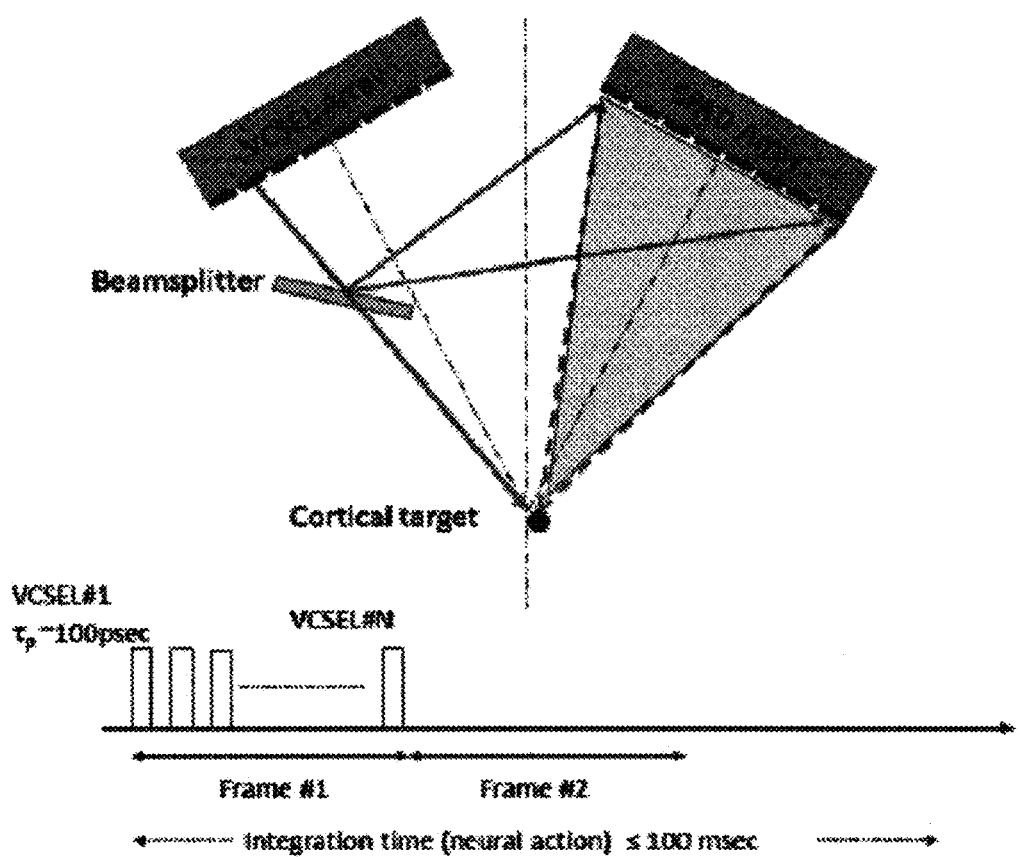
FIG. 5 is a block diagram of an exemplary optical MIMO NIR subsystem.

As shown in FIG. 5, we developed an optical MIMO NIR subsystem 50 for high spatiotemporal resolution (to 1 mm;

100 msec) in detecting brain activity from the cortex. Each individual VCSEL element emits 100 psec pulses on command which synchronize a high-speed single photon counting camera. We insert additional micro-optics to (a) create a reference beam and (b) narrow the field-of view, so as to perform at time-domain coherent imaging ("hologram") to detect mainly the brain-activity informative backscattered ballistic and sub-diffusive photons. A goal is to optimize the subsystem components 50 and to maximize a brain recording performance of an integrated, compact, wearable photonic platform.

The subsystem 50 integrates vertical-cavity surface-emitting lasers, single-photon avalanche photodiodes, and coherent detection techniques to enhance a spatial resolution, sensitivity/depth penetration, and chromophore quantification capabilities of a mobile NIRS device. More specifically, three main components are illustrated, i.e., a source of light, a cortical target and a detector. Here, the source of light is shown as a vertical-cavity surface-emitting laser (VCSEL) array, a type of semiconductor laser diode. The detector is shown as a single-photon avalanche diode (SPAD), a solid-state photodetector. A beam of light is directed towards a beamsplitter, causing some light to reflect off the cortical target and back to the detector and some light to head straight from the beamsplitter to the detector. The slight difference in receipt by the detector can be used produce a hologram. This sequence of generating light beams is preformed rapidly in real time and is used to generate a composite hologram, i.e., a summation of slightly different optical pathways reflecting from the cortical target at different angles. VCSEL array performance can support 100's of Watts of continuous wave optical output power and modulation bandwidth >10 GHz. The VCSEL arrays can have elements that are separated by as small as 20 μm spacing, in linear, hexagonal or other geometries.

Figure 6:
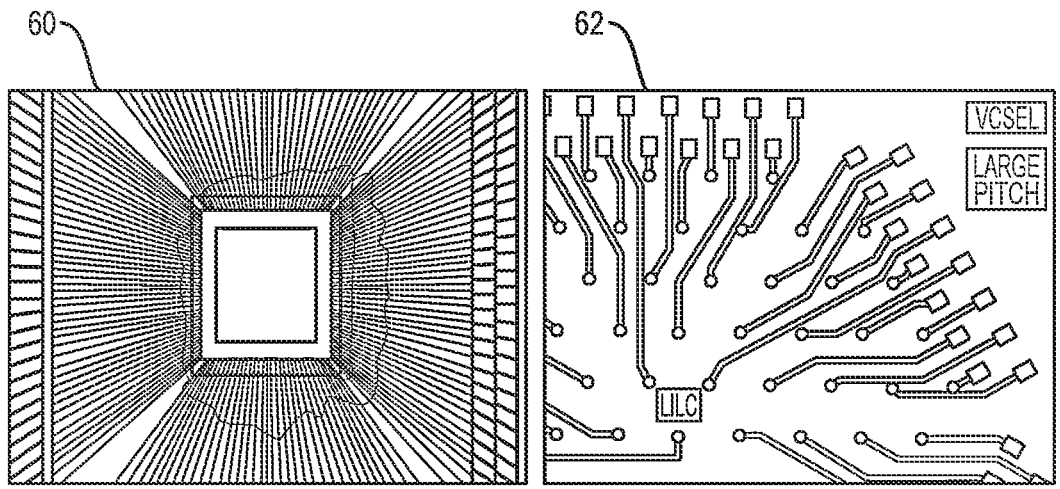
FIG. 6 illustrates two examples of 2-dimensional infrared VCSEL arrays.

In FIG. 6, two examples of two-dimensional (2D) infrared VCSEL arrays are illustrated, i.e., an array 60 on twenty packaged μm pitch (chip 64×64 is 12 matrix×10 mm) addressable and a eight-five element individually addressable VCSEL array 62 capable of >10 GHz bandwidth (chip is ×4 mm).

Referring again to FIG. 5, a VCSEL emission wavelength can be selected using appropriate active region semiconductor composition and through the design of the optical cavity dimension. For a given epitaxial VCSEL structure (i.e., epitaxial wafer), the lasing wavelength can be varied by approximately 20 nm. For this NIRS imaging application, we need 50 nm or greater wavelength difference. Thus, separate VCSEL epitaxial wafers are used to support output wavelengths.

Figure 7A:
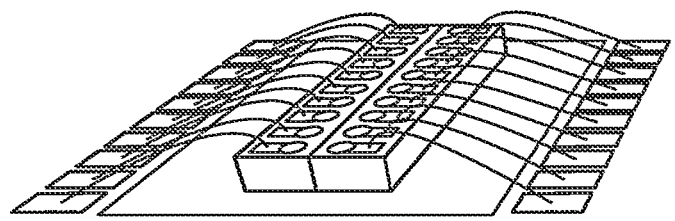
FIG. 7A illustrates an exemplary sketch of dual linear VCSEL arrays packaged chip-on-board via wire bonds.
Figure 7B:
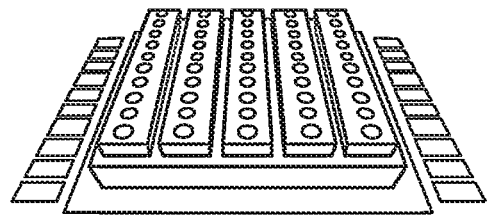
FIG. 7B illustrates an exemplary sketch of multiple VCSEL die and wavelengths flip-chip integrated.

We fabricated oxide-confined high efficiency VCSEL linear arrays using two epitaxial wafers to support two separate wavelengths suitable for hemodynamic neurovascular detection (780 nm and 850 nm). The VCSELs are designed to be capable of laser pulses ≤100 psec (i.e., less than the round-trip light propagation time from atop skull to cortical target and back). The linear arrays are designed to monolithically include up to 256 emitters on 40 μm pitch (i.e. 256 lasers within ≈1 cm). FIG. 7A illustrates an exemplary sketch of dual linear VCSEL arrays packaged chip-on-board via wire bonds while FIG. 7B illustrates an exemplary sketch of multiple VCSEL die and wavelengths flip-chip integrated. The dual wavelength closely aligned VCSEL arrays represent the individual "measurement unit cell" which can be replicated for whole-brain imaging. For a prototype NIRS unit, the two linear VCSEL arrays are packaged "chip-on-board" with wire-bonds to enable individual addressability, as required for the on-demand operation of each laser (see FIG. 5). The driver chips and high speed connectors need for signal input (not shown in FIGS. 7A and 7B) are also incorporated onto the source board.

The coherent, sub-nsec time gated coherent detection requires dual use of each VCSEL element of the array. While a major fraction of the laser power is directed into the scalp, a mW level remainder is waveguided directly to adjacent photodetector elements. This emission serves as the reference beam (local oscillator) in the coherent detection (=heterodyne detection) whereby a detector element mixes the two inputs of light returning from cortical targets and the time-coincident reference pulse. Nanoscale texture is embossed on surfaces of thin, transparent polyethylene sheets to control light propagation e.g. in both perpendicular and lateral (i.e. optical waveguide) directions.

Figure 8:
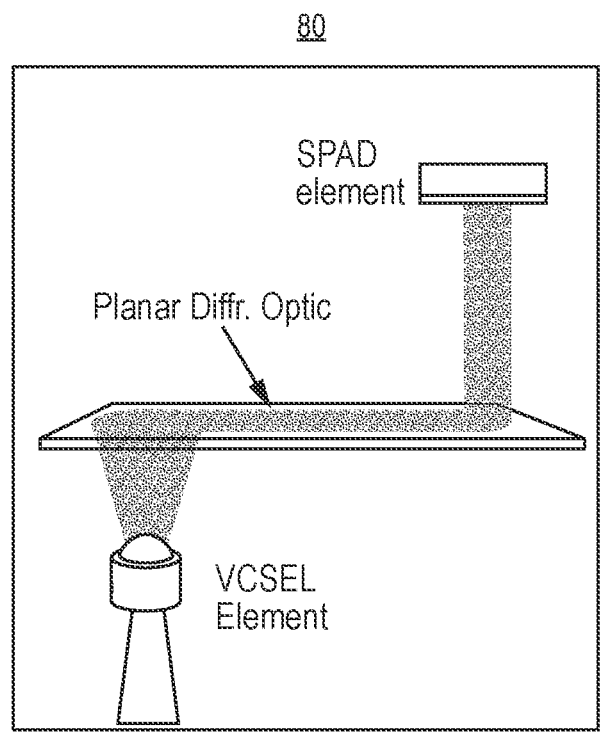
FIG. 8 shows an illustration of a configuration where such a diffractive optic is designed as a planar combination of input/output IR couplers and beamsplitters.
Figure 9:
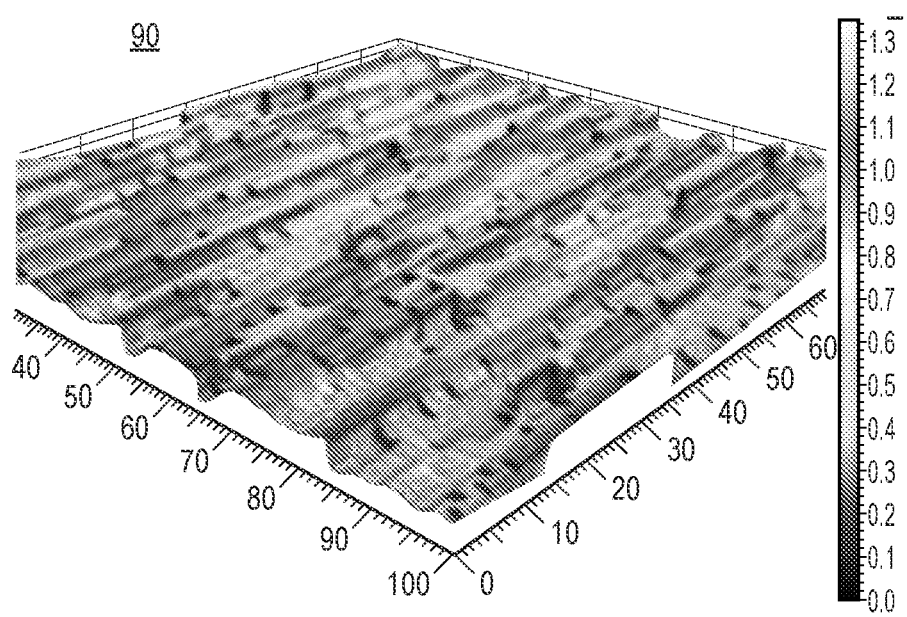
FIG. 9 illustrates an exemplary atomic force microscope image.

FIG. 8 shows an illustration of a configuration 80 where such a diffractive optic is designed as a planar combination of input/output IR couplers and beamsplitters. The planar structures, with programmable features to the nanoscale (atomic force microscope image 90 of FIG. 9), can also accommodate focusing/defocusing Fresnel lenses, which we use e.g. at the detector to limit the field of view (small numerical aperture for limited field of view FOV) for selective collection of ballistic and sub-diffusive photons from targeted depth in cortex.

Figure 10:
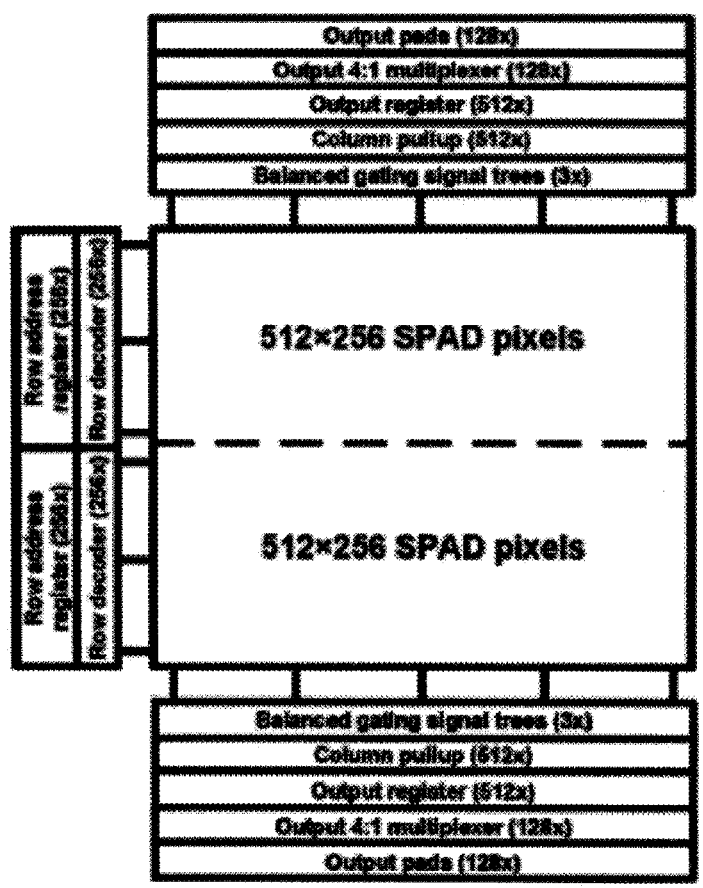
FIG. 10 illustrates an exemplary concentric-cylinder design of a dynamic layered phantom.

FIG. 10 illustrates an exemplary concentric-cylinder design of a dynamic layered phantom 100. The phantom 100 has a 60 mm radius with thin-film optical density filters to simulate skin and hair absorption. Scalp, brain and perturbation volumes are Intralipid plus porcine blood, circulated via separate infusion pumps, to independently and dynamically change optical properties of the scalp and brain regions. CSF is simulated with saline plus a small amount of Intralipid, and the skull layer is semi-solid (silicone mixed with carbon black and $TiO_2$). Absorption and scattering properties of each layer will match those of real tissue. Skull and brain compartments will be movable to independently vary thicknesses from 2-10 mm. Inside the brain region spherical chambers are attached on a translation stage (up to 80 mm travel). These "perturbations" have inner diameters ranging from 0.5-10 mm with 30% greater absorption than the surrounding medium, suspended by a thin, NA-neutral line. Step motors enable one to continuously vary the perturbation location, unlike with solid phantoms. Blood oxygenation changes will be controlled via a yeast-oscillation reaction in a mixing chamber prior to feeding the infusion pumps. All chambers are thin-wall (<0.5 mm) diffusive plastic that minimize numerical aperture, scattering and absorption deltas.

Figure 11:
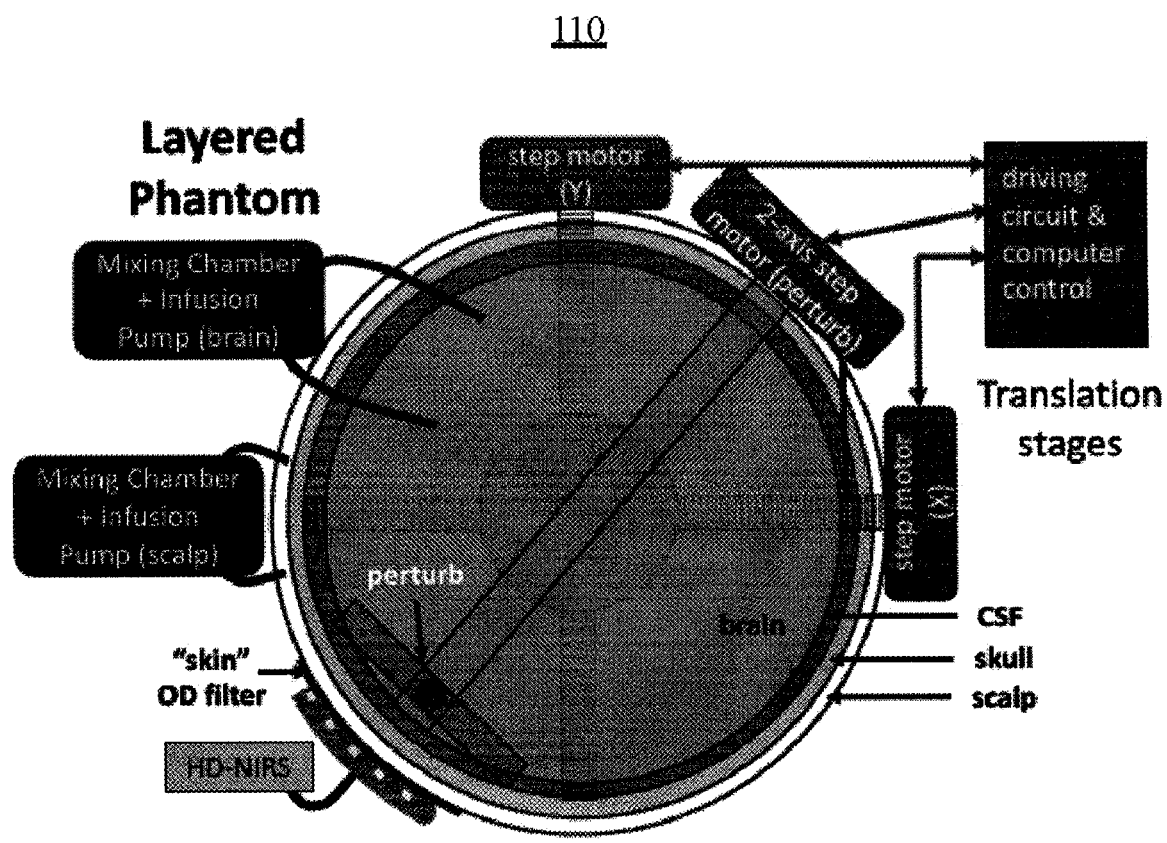
FIG. 11 illustrates a top view of an exemplary layered phantom design.

FIG. 11 is a top view of an exemplary layered phantom design 110 for depth and sensitivity testing of the NINscan-HSD prototype. Here, the sensor pad included a black, dense and moldable silicone to provide flexible but secure positioning of all optical components, with ~1 mm spacing between sources and detectors. This form was embedded in a larger pad that provides strain-relief for system wiring, as well as a Velcro®-based system for securing the pad to a headband for positioning over different head regions. For use through hair, we have used rounded lenses (e.g, Edmunds Optics) mounted over the surface of both lasers and detectors and add those when needed.

We characterized our system for detecting and quantifying functional brain activation and scattering changes in healthy adult volunteers. We focused on three target cortical regions located in different head regions and at different depths from the skin surface—primary visual, primary motor, and ventrolateral prefrontal cortex—conducting tests during three functional tasks.

In summary, the present invention integrates three major advances in state-of-the-art photonics: VCSELs, SPADs, and coherent detection techniques. We constructed an imaging system from the unique components to significantly enhance the spatial resolution, sensitivity/depth penetration, and chromophore quantification capabilities of mobile NIRS devices. This enhanced our understanding of the few-scattering-events, sub-diffuse photon propagation regime and is a revolutionary advance in mobile human brain imaging, as targeted by the BRAIN Initiative.

Although the present invention has been described in terms of a preferred embodiment, it will be appreciated that various modifications and alterations might be made by those skilled in the art without departing from the spirit and scope of the invention.

What is claimed is:

1. An ultra high-resolution near infrared (NIR) brain imager system comprising:
    a modular cap, the modular cap comprising:
        a first array of closely spaced vertical-cavity surface-emitting lasers (VCSELs), each said VCSEL in said array being individually addressable and configured to emit 100 psec NIR pulses, said first array being a two-dimensional array with spacing between VCSELs as low as about 20 μm; and
        a second array of single-photon avalanche photodiodes (SPADs), each said SPAD configured to detect said NIR pulses with sub-nanosecond time, each one of the VCSEL-SPAD modules comprising a two-dimensional (2D) VCSEL array and a SPAD detector array; and
    wherein said first and second arrays are adapted for multiple input-multiple output (MIMO) communications.

2. The system of claim 1 wherein the VCSEL-SPAD modules are arranged in a two-dimensional (2D) array.

3. The system of claim 2 wherein each SPAD detector is configured for about 20 psec time-gating.

4. The system of claim 3 wherein each VCSEL array provides an ultra-high-density, high-performance light source.

5. The system of claim 1, wherein said VCSELs emit pulses at wavelengths of about 780 nm and about 850 nm.

6. The system of claim 1, wherein each VCSEL is paired to a corresponding SPAD and are synchronized to provide a plurality of source-detector pairs in a volume of interest to generate a time-domain image, the time-domain image resulting from a summation of different optical pathways reflecting from the target tissue at different angles for a given VCSEL-SPAD pair.

* * * * *